United States Patent
Takahira

(10) Patent No.: US 10,252,959 B2
(45) Date of Patent: Apr. 9, 2019

(54) METHOD FOR PRODUCING FLUORINE-CONTAINING OLEFIN COMPOUND

(71) Applicant: AGC Inc., Tokyo (JP)

(72) Inventor: Yusuke Takahira, Tokyo (JP)

(73) Assignee: AGC Inc., Tokyo (JP)

( * ) Notice: Subject to any disclaimer, the term of this patent is extended or adjusted under 35 U.S.C. 154(b) by 0 days.

(21) Appl. No.: 15/694,392

(22) Filed: Sep. 1, 2017

(65) Prior Publication Data

US 2017/0369402 A1  Dec. 28, 2017

Related U.S. Application Data

(63) Continuation of application No. PCT/JP2016/056626, filed on Mar. 3, 2016.

(30) Foreign Application Priority Data

Mar. 3, 2015 (JP) .................... 2015-041644

(51) Int. Cl.
| | |
|---|---|
| C07C 17/26 | (2006.01) |
| C07C 17/263 | (2006.01) |
| C07C 17/35 | (2006.01) |
| C07C 17/37 | (2006.01) |
| C07C 17/06 | (2006.01) |
| C07B 61/00 | (2006.01) |

(52) U.S. Cl.
CPC .............. *C07C 17/06* (2013.01); *C07C 17/26* (2013.01); *C07C 17/263* (2013.01); *C07C 17/35* (2013.01); *C07C 17/37* (2013.01); *C07B 61/00* (2013.01)

(58) Field of Classification Search
CPC ....... C07C 17/37; C07C 17/26; C07C 17/263; C07C 17/35
See application file for complete search history.

(56) References Cited

U.S. PATENT DOCUMENTS

| | | | |
|---|---|---|---|
| 2016/0176791 A1 | 6/2016 | Takahira | |
| 2017/0101360 A1 | 4/2017 | Takahira | |

FOREIGN PATENT DOCUMENTS

| | | |
|---|---|---|
| WO | 2009/003085 | 12/2008 |
| WO | 2015/033927 | 3/2015 |

OTHER PUBLICATIONS

T. M. Trnka, et al. "Olefin Metathesis with 1,1-Difluoroethylene", Angew Chem. Int. Ed., No. 40. pp. 3441-3444. (2001).
A. K. Chatterjee, et al. "A General Model for Selectivity in Olefin Cross Metathesis", J. Am. Chem. Soc., No. 125, pp. 11360-11370, (2003).
S.J. Connon, et al. "Recent Developments in Olefin Cross-Metathesis", Angew. Chem. Int.E d., No. 42, pp. 1900-1923 (2003).
M. H. Lim, et al., "Synthesis of Novel D-2'-Deoxy-2'-C-difluoromethylene-4'-thiocytidine as a Potential Antitumor Agent", Org. Lett., No. 4, pp. 529-531, (2002).
MacNaughtan,M.L., Ruthenium-Catalyzed Metathesis With Directly Functionalized Olefins [online], 2009, [retrieval date May 17, 2016 (May 17, 2016)]. https://deepblue.lib.umich.edu/bitstream/handle/2027.42/63649/mlmac_1.pdf?seauence=1&isAllowed=y.
Y. Tkahira, et al., "Ruthenium-Catalyzed Olefin Cross-Metathesis with Tetrafluoroethylene and Analogous Fluoroolefins", J. Am. Chem. Soc., No. 137, pp. 7031-7034, (2015).

*Primary Examiner* — Medhanit W Bahta
(74) *Attorney, Agent, or Firm* — Oblon, McClelland, Maier & Neustadt LLP

(57) ABSTRACT

A method for producing at least one compound of a fluorine-containing olefin compound (51) or a fluorine-containing olefin compound (52) includes performing a reaction of a fluorine-containing olefin compound (21) with an olefin compound (31) in the presence of a metal-carbene complex compound having an olefin metathesis reaction activity and an olefin compound (41) or (42).

[Chem. 1]

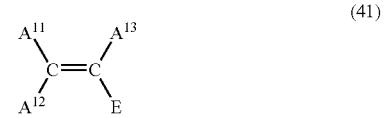

(41)

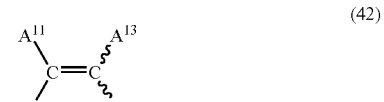

(42)

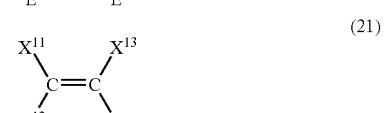

(21)

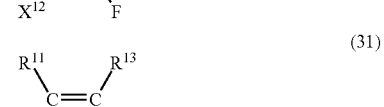

(31)

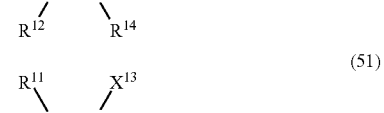

(51)

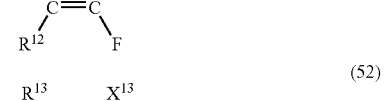

(52)

14 Claims, No Drawings

METHOD FOR PRODUCING FLUORINE-CONTAINING OLEFIN COMPOUND

TECHNICAL FIELD

The present invention relates to a novel method for producing a fluorine-containing olefin compound through olefin metathesis reaction.

Among olefin compounds where a part or all of hydrogen atoms are substituted with fluorine atoms, that is, fluorine-containing olefin compounds, some industrially-useful compounds are known. For example, 1,1,2-trifluoro-2-substituted olefins such as 1,1,2-trifluorostyrene are compounds useful as organic synthetic building blocks, monomers for polymerization, materials for polymer electrolytes, and the like, and 1,1-difluoro-2,2-disubstituted olefins are compounds useful as materials for medicines such as enzyme inhibitors, for ferroelectric materials and the like. However, no method for simply and efficiently producing these compounds has been established yet. For example, Non-Patent Document 1 reports production of 1,1-difluoro-2,2-disubstituted olefins through Wittig reaction of carbonyl compounds (difluoromethylidenation). However, in the case where the carbonyl compound is a ketone, the yield is low even if an excessive amount (4 to 5 equivalents or more) of Wittig reagent is used, and further, as a phosphorus compound, a carcinogenic hexamethylphosphorous triamide must be used.

Consequently, if other fluorine-containing olefins (e.g., 1,1-difluoro-2,2-disubstituted olefins, etc.) could be simply and efficiently produced from industrially-easily-available fluorine-containing olefins such as tetrafluoroethylene or hexafluoropropylene, the method could be an extremely useful synthesis method as compared with already-existing methods.

On the other hand, olefin metathesis reaction that is a double bond recombination reaction with a metal catalyst (hereinafter this may be simply referred to as "olefin metathesis") is widely utilized as a production method for olefins having various types of substituents. However, electron-deficient olefins having an electron-withdrawing substituent have low reactivity, and therefore use thereof in olefin metathesis is not easy. For example, Non-Patent Document 2 investigates the reactivity of olefins having various substituents and describes that the reactivity of electron-deficient olefins is low. In fact, olefins having a halogen such as a fluorine atom or a chlorine atom are electron-deficient olefins, and therefore there are few reports using them in olefin metathesis. For example, in Non-Patent Document 3, olefin metathesis of a ruthenium complex and vinylidene fluoride (i.e. 1,1-difluoroethylene) is investigated, but the report describes that the expected products, that is, ethylene and tetrafluoroethylene could not be obtained at all. In that manner, use of halogen atom-containing olefins in olefin metathesis is not practicable. Above all, tetrafluoroethylene and hexafluoropropylene are useful compounds from the viewpoint of industrial easy availability and commercialization; however, these are not only extremely electron-deficient olefins but also difficult to handle, and therefore there has been no report relating to use thereof in olefin metathesis.

PRIOR ART DOCUMENTS

Non-Patent Documents

Non-Patent Document 1: Lim, M. H. et al., Org. Lett., 2002, 4, 529-531.

Non-Patent Document 2: Chatterjee, A. K. et al., J. Am. Chem. Soc., 2003, 125, 11360-11370.

Non-Patent Document 3: Trnka, T. et al., Angew. Chem. Int. Ed., 2001, 40, 3441-3444.

SUMMARY OF THE INVENTION

Problem that the Invention is to Solve

Accordingly, an object of the present invention is to provide a method for producing other fluorine-containing olefins in a simplified manner and efficiently from industrially-easily-available fluorine-containing olefins such as tetrafluoroethylene or hexafluoropropylene through olefin metathesis.

Means for Solving the Problem

The present inventors diligently made investigations and, as a result, have discovered that in the case where a metathesis reaction of an olefin containing a fluorine atom (a fluorine-containing olefin) with another olefin is conducted in the presence of a metal catalyst having a metal-carbon double bond and further in the presence of an olefin having a specific substituent during the metathesis reaction, the metathesis reaction is accelerated under mild conditions and a fluorine-containing olefin can be obtained more efficiently. The present invention has been thus completed.

The present invention relates to the following <1> to <11>.

<1> A method for producing at least one compound of a fluorine-containing olefin compound represented by the following formula (51) or a fluorine-containing olefin compound represented by the following formula (52), the method including performing a reaction of a fluorine-containing olefin compound represented by the following formula (21) with an olefin compound represented by the following formula (31); in the presence of a metal-carbene complex compound (10) having an olefin metathesis reaction activity and a compound represented by the following formula (41) or in the presence of the metal-carbene complex compound (10) and an olefin compound represented by the following formula (42).

[Chem. 1]

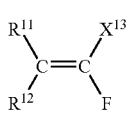

(51)

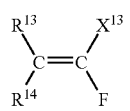

(52)

In the formulae, the symbols represent the following meanings.

$A^{11}$ and $A^{12}$ are each independently a group selected from the group consisting of the following group (i), group (iia), group (iii), and group (iv). $A^{11}$ and $A^{12}$ may bond to each other to form a ring. In the case where one of $A^{11}$ or $A^{12}$ is a halogen atom, the other is a group selected from the group consisting of the group (i), the group (iii), and the group (iv).

$A^{13}$ is a group selected from the group consisting of the following group (i), group (iii), and group (iv).

E is a group selected from the group consisting of —OR', —OSiR'$_3$, —NR'$_2$, —SR', and the following group (iia), and the R's are each independently a group selected from the group consisting of the following group (i), group (v), and group (vi). $A^{13}$ and E may bond to each other to form a ring.

$X^{11}$ and $X^{12}$ are each independently a group selected from the group consisting of the following group (i), group (ii), group (v), and group (vi). $X^{11}$ and $X^{12}$ may bond to each other to form a ring.

$X^{13}$ is a group selected from the group consisting of the following group (ii), group (v), and group (vi).

$R^{11}$ to $R^{14}$ are each independently a group selected from the group consisting of —H, —CH$_2$R, —CH(CR$_3$)$_2$, —C(CR$_3$)$_3$, and —Ar, wherein the Rs are each independently a group selected from the group consisting of a hydrogen atom, an alkyl group having a carbon number of from 1 to 12, and an alkyl group having a carbon number of from 1 to 12 and having an etheric oxygen atom between carbon atoms, and Ar is an aryl group having a carbon, number of from 5 to 12. $R^{11}$ and $R^{12}$ may bond to each other to form a ring. $R^{13}$ and $R^{14}$ may bond to each other to form a ring.

Group (i): a hydrogen atom.
Group (ii): a halogen atom.
Group (iia): a chlorine atom, a bromine atom, or an iodine atom.
Group (iii): a monovalent hydrocarbon group having a carbon number of from 1 to 20.
Group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.
Group (v): a group selected from the group consisting of an alkyl group having a carbon number of from 1 to 12, an alkoxy group having a carbon number of from 1 to 12, an aryl group, having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.
Group (vi): the group (v) further containing one or more atoms selected from the group consisting of an oxygen atom, a nitrogen atom, a sulfur atom, a phosphorus atom, and a silicon atom.

<2> The production method according to above <1>, wherein an olefin compound represented by the formula (41) or the formula (42) is any of compounds represented by the following formulae. In the formulae, the R's are each independently a group selected from the group consisting of the group (i), group (v), and group (vi).

[Chem. 2]

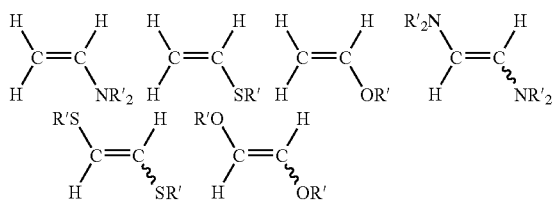

<3> The production method according to above <1> or <2>, wherein $X^{13}$ in the fluorine-containing olefin compound represented by the formula (21) is a halogen atom or a perhalogenated alkyl group having a carbon number of from 1 to 8.

<4> The production method according to any one of above <1> to <3>, wherein a metal in the metal-carbene complex compound (10) is ruthenium, molybdenum, or tungsten.

<5> The production method according to any one of above <1> to <4>, wherein a metal in the metal-carbene complex compound (10) is ruthenium.

<6> The production method according to any one of above <1> to <4>, wherein a metal in the metal-carbene complex compound (10) is molybdenum or tungsten and the metal-carbene complex compound (10) has an imide ligand and a ligand including two coordinating oxygen atoms as a ligand [L].

<7> The production method according to any one of above <1> to <6>, wherein in the olefin compound represented by the formula (21), $X^{11}$ is group (i), group (ii), group (v), or group (vi), $X^{12}$ is group (i), group (ii), group (v), or group (vi), and $X^{13}$ is group (ii), group (v) or group (vi). The above group (i), group (ii), group (v), and group (vi) have the same meanings as in above <1>.

<8> The production method according to any one of above <1> to <7>, wherein the olefin compound represented by the formula (21) is a 1,1-difluoroolefin.

<9> The production method according to any one of above <1> to <8>, wherein the olefin compound represented by the formula (21) is at least one kind of olefin compound selected from olefin compounds represented by the following formulae.

[Chem. 3]

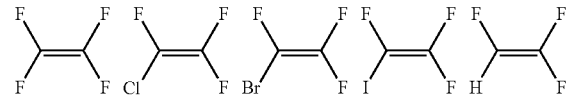

-continued

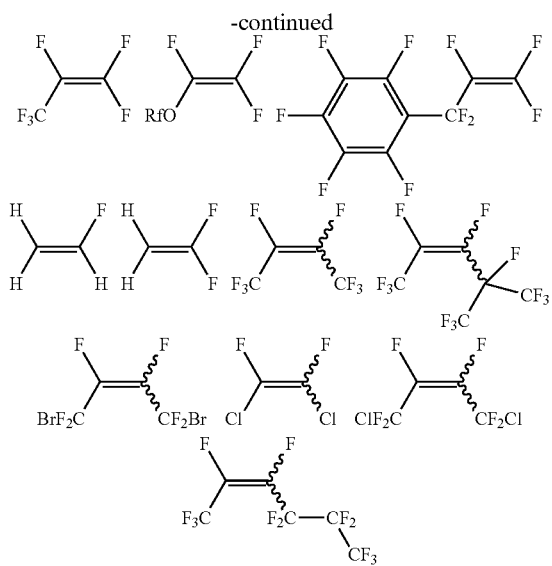

In the formulae, Rf is a (per)fluorinated alkyl group having a carbon number of from 1 to 20, a (per)fluorinated alkyl group having a carbon number of from 1 to 20 and having an etheric oxygen atom between a carbon atom and a carbon atom, or a (per)fluorinated aryl group having a carbon number of from 5 to 20.

<10> The production method according to any one of above <1> to <9>, wherein the temperature of the reaction is from 0 to 150° C.

<11> The production method according to any one of above <1> to <10>, wherein no solvent is used for the reaction.

Effect of the Invention

According to the production method for a fluorine-containing olefin compound of the present invention, the reaction is more apt to proceed than a conventional metathesis reaction and a different fluorine-containing olefin compound can be produced easily and highly efficiently from a fluorine-containing olefin and another olefin.

Modes for Carrying Out the Invention

The present invention is explained below in detail. The present invention should not be construed as being limited to the following embodiments, and can be modified at will unless the modifications depart from the spirit of the invention. The present invention relates to metathesis performed with the aid of a metal catalyst, and there are cases where explanations on general features common to conventional techniques are omitted.

In this description, there are cases where "a compound represented by formula (X)" is simply referred to as "a compound (X)".

In the description, the perhalogenated alkyl group means an alkyl group which all hydrogen atoms of the alkyl group have been substituted with halogen atoms. The perhalogenated alkoxy group means an alkoxy group in which all hydrogen atoms of the alkoxy group have been substituted with halogen atoms. The same applies to the perhalogenated alkoxy group and the perhalogenated an group.

The (per)halogenated alkyl group is a general term for both a halogenated alkyl group and a perhalogenated group.

Namely, this group is an alkyl group having one or more halogen atoms. The same applies to the (per)halogenated alkoxy group, (per)halogenated aryl group, and (per)halogenated aryloxy group.

The term aryl group means a monovalent group corresponding to a residue derived by removing one hydrogen atom bonding to any one carbon atom in the carbon atoms forming an aromatic ring in an aromatic compound. The term is used as a general term including an aryl group derived from a carbocyclic compound and a heteroaryl group derived from a heterocyclic compound.

The carbon number of the hydrocarbon group means the total number of the carbon atoms contained in the whole hydrocarbon group. In the case where the group has no substituent, the carbon number means the number of the carbon atoms which constitute the hydrocarbon framework. In the case where the group has a substituent, the carbon number means the sum of the number of the carbon atoms which constitute the hydrocarbon framework and the number of the carbon atoms of the substituent.

Incidentally, wavy lines in a chemical formula indicate that the compound is either of E/Z isomers or is a mixture of both.

The heteroatom means an atom which is neither a carbon atom nor a hydrogen atom. Preferred are one or more kinds of atoms selected from the group consisting of an oxygen atom, a nitrogen atom, a sulfur atom, a phosphorus atom, a silicon atom, and a halogen atom. More preferred is an oxygen atom or a nitrogen atom.

Reaction Mechanism

The present invention relates to a method for producing a fluorine-containing olefin through an olefin metathesis reaction. For example, as shown by the following scheme (a), a fluorine-containing olefin compound represented by the formula (21) and an olefin compound represented by the formula (31) are subjected to the olefin metathesis reaction in the presence of a metal-carbene complex compound (10) (catalyst) and an olefin compound represented by the formula (41) to obtain a fluorine-containing olefin compound represented by the formula (51).

In the case where the compound (21) and the compound (31) are subjected to the metathesis reaction in the presence of a catalyst, depending on structures of substituents of the compound (31), the reaction step for obtaining an unstable reaction intermediate ([L]M=CR$^{13}$R$^{14}$) from an very stable reaction intermediate ([L]M=CFX$^{13}$) does not proceed. Because of this, reactions in CYCLE A shown in Scheme 1, are less apt to occur, and the compound (51) is exceedingly difficult to obtain.

Accordingly, by causing compound (41) to be present in the system, it is possible to obtain the unstable reaction intermediate ([L]M=CR$^{13}$R$^{14}$) from the very stable reaction intermediate ([L]M=CFX$^{13}$) via a stable reaction intermediate ([L]M=CEA$^{13}$). Thus, reactions in CYCLE B and CYCLE C proceed, and the compound (51) can be obtained (Scheme 2).

It is presumed that the difference in reaction progress is due to the relative energy levels of the reaction intermediates.

That is, it is thought that in the case where the difference in energy level between the very stable reaction intermediate ([L]M=CFX$^{13}$) and the unstable reaction intermediate ([L]M=CR$^{13}$R$^{14}$) is too large, the reaction for converting the unstable reaction intermediate ([L]M=CR$^{13}$R$^{14}$) into the very stable reaction intermediate ([L]M=CFX$^{13}$) proceeds but the reverse reaction is less apt to proceed (CYCLE A). Hence, conversion of the very stable reaction intermediate ($[L]M=CFX^{13}$) into the unstable reaction intermediate ($[L]M=CR^{13}R^{14}$) is made via a stable reaction intermediate ($[L]M=CEA^{13}$), resulting in reduced differences in energy level. As a result, a reaction for converting the very stable reaction intermediate ($[L]M=CFX^{13}$) into the stable reaction intermediate ($[L]M=CEA^{13}$) proceeds, and a reaction for converting the stable reaction intermediate ($[L]M=CEA^{13}$) into the unstable reaction intermediate ($[L]M=CR^{13}R^{14}$) then proceeds (CYCLE B and CYCLE C). Because of this, cyclic reactions between the very stable reaction intermediate ($[L]M=CFX^{13}$) and the unstable reaction intermediate ($[L]M=CR^{13}R^{14}$) appear to occur, and the metathesis reaction between the compound (21) and the compound (31) proceeds to make it possible to obtain the compound (51).

Namely, in the series of reactions shown in Scheme 2., the compound (51) is formed from the compound (21) and the compound (31) in the presence of a catalyst through a reaction with the compound (41) or with a compound (41)' derived from the compound (41). The compound (41)' is formed through a reaction in CYCLE C and subjected to a reaction in CYCLE B, and is hence thought to function like a catalyst. The same applies in the case of using the compound (42) in place of the compound (41).

As explained above, in cases where the metathesis reaction between compound (21) and compound (31) is less apt to occur, the metathesis reaction between the compound (21) and the compound (31) can be made to proceed by causing the compound (41) or the compound (42) to exist therewith, thereby making it possible to obtain the desired compound (51). One kind of compound (41) or compound (42) may be used, or two or more kinds of compounds (41) and (42) may be used.

In the case of producing the compound (52) which will be described later, the reaction is thought to proceed by the same reaction mechanism as described above.

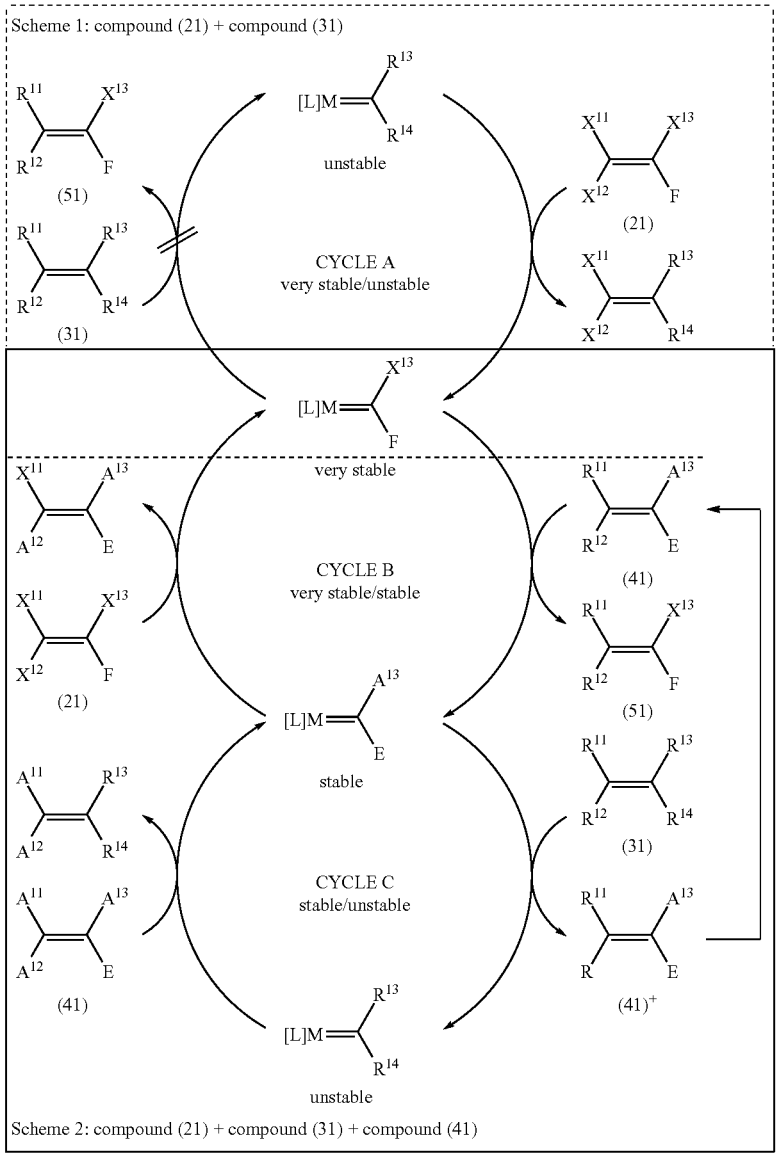

In the description, the symbols in the formulae have following meanings.

[L] is a ligand.

M is ruthenium, molybdenum, or tungsten.

$A^{11}$ and $A^{12}$ are each independently a group selected from the group consisting of the following: group (i), group (iia), group (iii), and group (iv), $A^{11}$ and $A^{12}$ may bond to each other to form a ring. In the case where one of $A^{11}$ or $A^{12}$ is a halogen atom, the other is a group selected from the group consisting of the group (i) the group (iii), and the group (iv).

$A^{13}$ is a group selected from the group consisting of the following group (i), group (iii), and group (iv).

E is a group selected from the group consisting of —OR', —OSiR'$_3$, —NR'$_2$, —SR', and the following group (iia), and the R's are each independently a group selected from the group consisting of the following group (i), group (v), and group (vi). $A^{13}$ and E may bond to each other to form a ring.

$X^{11}$ and $X^{12}$ are each independently a group selected from the group consisting of the following group (i), group (ii), group (v), and group (vi). $X^{11}$ and $X^{12}$ may bond to each other to form a ring.

$X^{13}$ is a group selected from the group consisting of the following group (ii), group (v), and group (vi).

$R^{11}$ to $R^{14}$ are each independently a group selected from the group consisting of —H, —CH$_2$R, —CH(CR$_3$)$_2$, —C(CR$_3$)$_3$, and —Ar, wherein the Rs are each independently a group selected from the group consisting of a hydrogen atom, an alkyl group having a carbon number of from 1 to 12, and an alkyl group having a carbon number of from 1 to 12 and having an etheric oxygen atom between carbon atoms, and Ar is an aryl group having a carbon number of from 5 to 12. $R^{11}$ and $R^{12}$ may bond to each other to form a ring. $R^{13}$ and $R^{14}$ may bond to each other to form a ring.

Group (i): a hydrogen atom.

Group (ii): a halogen atom.

Group (iia): a chlorine atom, a bromine atom, or an iodine atom.

Group (iii): a monovalent hydrocarbon group having a carbon number of from 1 to 20, Group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

Group (v): a group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.

Group (vi): the group (v) further containing one or more atoms selected from the group consisting of an oxygen atom, a nitrogen atom, a sulfur atom, a phosphorus atom, and a silicon atom.

The group (v) is excluded from the group (vi).

The metathesis reaction is reversible. Namely, in Scheme (a), there are reverse reactions (reactions indicated by reverse arrows). However, a detailed explanation thereon is omitted. There is a possibility that the formed fluorine-containing olefin might include geometrical isomers. However, an explanation thereon is omitted because it strongly depends on the individual reactions.

The present invention is characterized in that, as shown in the following Scheme (b), for example, the compound (21) and the compound (31) are subjected to the metathesis reaction in the presence of the compound (11) and the compound (41), thereby producing at least one of the compound (51) and, the compound (52). The same results are obtained in the case of using the compound (42) in place of the compound (41).

The metathesis reaction proceeds in the presence of a metal-carbene complex compound (10). The compound (11) is described as a representative example of the metal-carbene complex compound (10), and $A^1$ and $A^2$ in the formula will be described later.

Examples of the metal-carbene complex compound (10) include a ruthenium-carbene complex, a molybdenum-carbene complex, or a tungsten-carbene complex (hereinafter, these may be also referred to as "metal-carbene complexes"). Besides the compound (11), the metal-carbene complex may be the following compound (12), compound (13), compound (14), compound (15), compound (16), and compound (17). It is thought that in the case of using any of these complexes, the metathesis reaction proceeds by the same reaction mechanism as in Scheme (a) described above. The same applies to the following metal-carbene complexes. The symbols in the following formulae have the same meanings as those described above.

[Chem. 5]

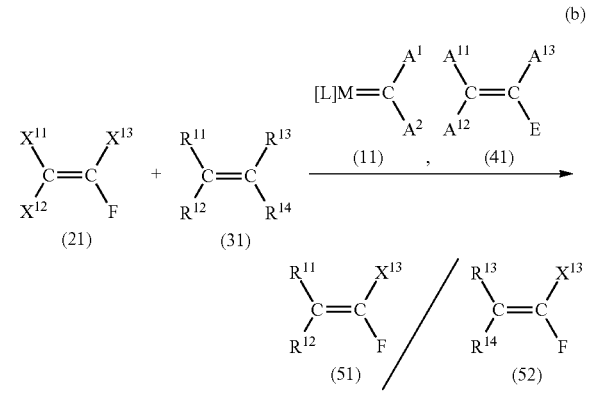

[Chem. 6]

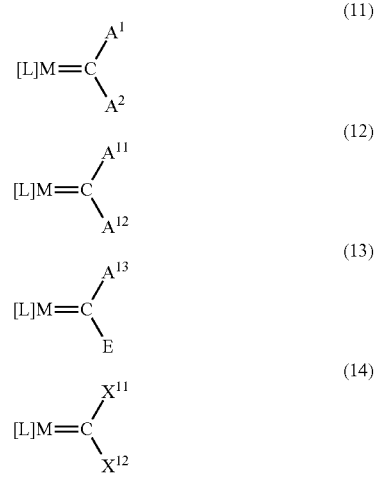

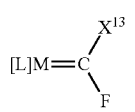

(15)

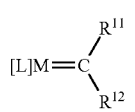

(16)

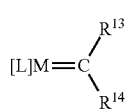

(17)

<Metal-Carbene Complex Compound (10) Having Olefin Metathesis Reaction Activity>

The metal-carbene complex compound (10) is explained using the compound (11) as an example. The compound (11) serves as a catalyst in the production method according to the present invention and means both one charged as a reagent and one formed during the reaction (catalytically active species). Known as the compound (11) is one which comes to exhibit catalytic activity upon dissociation of some of the ligands under the reaction conditions and one which exhibits catalytic activity without dissociation of ligands, and any of these is employable in the present invention with no limitation. Since olefin metathesis generally proceeds with repeating olefin coordination to and dissociation from the catalyst, it is not always clear as to how many ligands other than olefins coordinate to the catalyst during the reaction. Consequently, in the description, [L] is not construed as specifying the number or kind of ligands. It is preferable that the metal in the metal-carbene complex compound (10) should be ruthenium, molybdenum, or tungsten.

It is preferable in the present invention that the reaction should be conducted in the presence, of at least one kind of metal-carbene complex compound selected from the group consisting of compound (11), compound (12), compound (13), compound (14), compound (15), compound (16, and compound (17). Preferred as the metal-carbene complex compound for use at the time of reaction initiation is the compound (11) from the viewpoint of availability and reaction efficiency.

The compound (11) is explained below in detail.

$A^1$ and $A^2$ in compound (11) are each independently a hydrogen atom, a halogen atom, a monovalent hydrocarbon group having a carbon number of from 1 to 20, or a monovalent hydrocarbon group having a carbon number of from 1 to 20 and containing one or more atoms selected from the group consisting of an oxygen atom, a nitrogen atom, a sulfur atom, a Phosphorus atom, and a silicon atom. $A^1$ and $A^2$ may bond, as a divalent group formed by removing one hydrogen or halogen atom, to each other to form a ring. The case where both $A^1$ and $A^2$ are halogen atoms is excluded from compound (11).

Examples of the halogen atoms include a fluorine atom, a chlorine atom, a bromine atom, and an iodine atom. A fluorine atom and a chlorine atom are preferred from the viewpoint of availability.

The monovalent hydrocarbon group having a carbon number of from 1 to 20 is preferably an alkyl group having a carbon number of from 1 to 20 or an aryl group having a carbon number of from 5 to 20, and may be linear, branched, or cyclic.

Preferred examples of the monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom include an alkyl group having a carbon number of from 1 to 20 and containing the atoms, an alkoxy group having a carbon number of from 1 to 20, aryl groups having a carbon number of from 5 to 20 and containing the atoms, and aryloxy groups having a carbon number of from 5 to 20. The monovalent hydrocarbon group may be linear, branched, or cyclic. In these preferred groups, a halogen atom may bond to at least a part of the carbon atoms. Namely, the monovalent hydrocarbon group may be, for example, a (per)fluoroalkyl group or a (per)fluoroalkoxy group. These preferred groups may have an etheric oxygen atom between a carbon atom and a carbon atom. Further, these preferred groups may have a substituent containing one or more atoms selected from the group consisting of a halogen atom, an oxygen atom, a nitrogen atom, a sulfur atom, a phosphorus atom, and a silicon atom. Examples of the substituent include a hydroxyl group, an amino group, an imino group, a nitrile group, an amido group (a carbonylamino group), a carbamate group (an oxycarbonylamino group), a nitro group, a carboxyl group, an ester group (an acyloxy group or an alkoxycarbonyl group), a thioether group, and a silyl group. These groups may be further substituted with an alkyl group or an aryl group. For example, the amino group (—NH—) may be a monoalkylamino group (—NHR), a monoarylamino group (—NHAr), a dialkylamino group (—$NR_2$), or a diarylamino group (—$NAr_2$). R is an alkyl group having a carbon number of from 1 to 12 or an alkyl group having a carbon number of from 1 to 12 and having an etheric oxygen atom between a carbon atom and a carbon atom, and Ar is an aryl group having a carbon number of from 5 to 12.

Preferred examples of the compound (11) having a combination of these $A_1$ and $A_2$ include one represented by the following formula, from the viewpoint of the availability thereof. In the following formulae, Cy means a cyclohexyl group.

[Chem. 7]

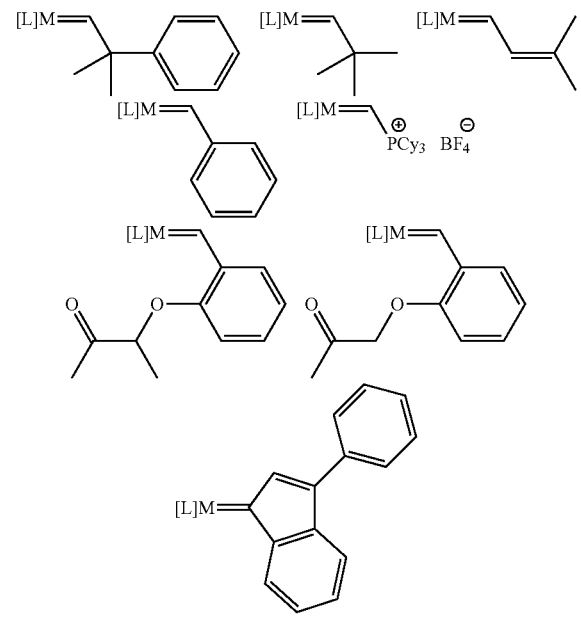

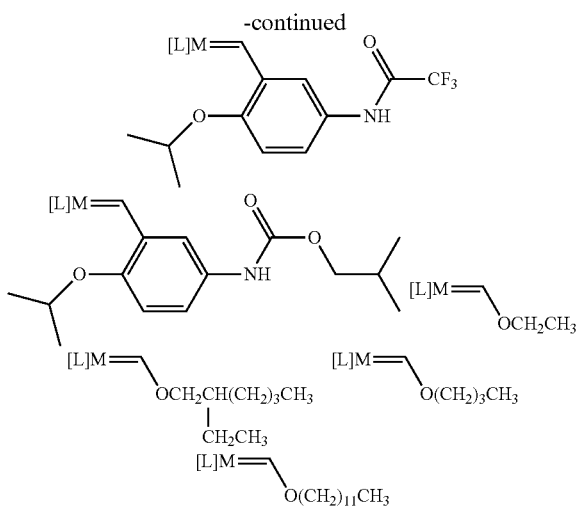

In the present invention, it is preferable that the metal in the metal-carbene complex is ruthenium.

Specifically, in the case where M is ruthenium in the compound (11), it can be represented by the following formula (11-A). The ligand [L] in the formula (11) is represented by $L^1$, $L^2$, $L^3$, $Z^{11}$, and $Z^{12}$ in the formula (11-A). The positions of $L^1$, $L^2$, $L^3$, $Z^{11}$, and $Z^{12}$ are not specifically defined, and these may be alternated to each other in the formula (11-A). That is, for example, $Z^{11}$ and $Z^{12}$ may be at the trans-position or at the cis-position.

[Chem. 8]

(11-A)

In the formula (11-A), $L^1$, $L^2$ and $L^3$ are each independently a ligand that has a neutral charge when dissociated from the metal center (a neutral electron-donating ligand). Specifically, examples thereof include a carbonyl group, amines, imines, pyridines, ethers, nitrites, esters, phosphines, thioethers, sulfoxides, sulfones, aromatic compounds, olefins, isocyanides, thiocyanates, heteroatom-containing carbene compounds, and the like. Of those, preferred are phosphines, pyridines and heteroatom-containing carbene compounds, and more preferred are trialkyl phosphines and N-hetero-cyclic carbene compounds.

However, depending on the combination of the above-mentioned ligands, all ligands could not coordinate with the metal center owing to steric factors and/or electronic factors, and as a result, some coordination positions may be vacant sites. For example, $L^1$, $L^2$ and $L^3$ include the following combinations.

$L^1$: a heteroatom-containing carbene compound, $L^2$: a phosphine, $L^3$: vacant (vacant coordination site).

$L^1$: a heteroatom-containing carbene compound, $L^2$: a pyridine, $L^3$: a pyridine.

In the formula (11-A), $Z^{11}$ and $Z^{12}$ are each independently a ligand that has a negative charge when dissociated from the metal center (anionic ligand). Specifically, examples thereof include a halogen atom, a hydrogen atom, a substituted diketonate group, a substituted cyclopentadienyl group, an alkyl group having a carbon number of from 1 to 20, an aryl group having a carbon number of from 5 to 20, a substituted alkoxy group having a carbon number of from 1 to 20, a substituted aryloxy group having a carbon number of from 5 to 20, a substituted carboxylate group having a carbon number of from 1 to 20, a substituted arylcarboxylate group having a carbon number of from 6 to 20, a substituted alkylthiolate group having a carbon number of from 1 to 20, a substituted arylthiolate group having a carbon number of from 6 to 20, a nitrate group, and the like. Above all, preferred is a halogen atom, and more preferred is a chlorine atom.

In the formula (11-A), $A^1$ and $A^2$ are the same as $A^1$ and $A^2$ in the formula (11), respectively.

From 2 to 6 of $L^1$, $L^2$, $L^3$, $Z^{11}$, $Z^{12}$, $A^1$, and $A^2$ may bond to each other to form a polydentate ligand.

The above-mentioned catalyst is generally referred to as "ruthenium-carbene complex", and, for example, ruthenium-carbene complexes described in Vougioukalakis, G. C. et al., Chem. Rev., 2010, 110, 1746-1787 can be used. Also for example, ruthenium-carbene complexes commercially available from Aldrich or Umicore are also usable.

Specific examples of the ruthenium-carbene complex include bis(triphenylphosphine)benzylidene ruthenium dichloride, bis(tricyclohexylphosphine)benzylidene ruthenium dichloride, bis(tricyclohexylphosphine)-3-methyl-2-butenylidene ruthenium dichloride, (1,3-diisopropylimidazol-2-ylidene)(tricyclohexylphosphine)benzylidene ruthenium dichloride, (1,3-dicyclohexylimidazol-2-yldene)(tricyclohexylphosphine)benzylidene ruthenium dichloride, (1,3-dimesitylimidazol-2-ylidene)(tricyclohexylphosphine)benzylidene ruthenium dichloride, (1,3-dimesityl-4,5-dihydroimidazol-2-ylidene)(tricyclohexylphosphine)benzylidene ruthenium dichloride, [1,3-bis(2,6-diisopropylphenyl)-4,5-dihydroimidazol-2-ylidene](tricyclohexylphosphine)benzylidene ruthenium dichloride, [1,3-bis(2-methylphenyl)-4,5-dihydroimidazol-2-ylidene](tricyclohexylphosphine)benzylidene ruthenium dichloride, [1,3-dicyclohexyl-4,5-dihydroimidazol-2-ylidene](tricyclohexylphosphine)benzylidene ruthenium dichloride, bis(tricyclohexylphosphine)ethoxymethylidene ruthenium dichloride, (1,3-dimesityl-4,5-dihydroimidazol-2-ylidene)(tricyclohexylphosphine)ethoxymethylidene ruthenium dichloride, (1,3-dimesityl-4,5-dihydroimidazol-2-ylidene)[bis(3-bromopyridine)]benzylidene ruthenium dichloride, (1,3-dimesityl-4,5-dihydroimidazol-2-ylidene)(2-isopropoxyphenylmethylidene) ruthenium dichloride, (1,3-dimesityl-4,5-dihydroimidazol-2-ylidene)[(tricyclohexylphosphoranyl)methylidene] dichlororuthenium tetrafluoroborate, UmicoreM2, UmicoreM51, UmicoreM52, UmicoreM71SIMes, UmicoreM71SIPr, UmicoreM73SIMes, UmicoreM73SIPr, and the like. Especially preferred are (1,3-dimesityl-4,5-dihydroimidazol-2-ylidene)(tricyclohexylphosphine)benzylidene ruthenium dichloride, (1,3-dimesityl-4,5-dihydroimidazol-2-ylidene)(2-isopropoxyphenylmethylidene) ruthenium dichloride, (1,3-dimesityl-4,5-dihydroimidazol-2-ylidene)[(tricyclohexylphosphoranyl)methylidene] dichlororuthenium tetrafluoroborate, UmicoreM51, UmicoreM52, UmicoreM71SIMes, UmicoreM71SIPr, UmicoreM73SIMes, and UmicoreM73SIPr. Of the above-mentioned complexes, the names starting from "Umicore" are trade names of the products by Umicore.

The above-mentioned ruthenium-carbene complexes may be used either singly or used in combination of two or more kinds thereof. Further if desired, these may be used as immobilized by a carrier such as silica gel, alumina, polymer or the like.

It is preferable in the invention that the metal of the metal-carbene complex compound should be molybdenum or tungsten, from the viewpoint of the availability of the catalyst.

In the case where M in compound (11) is molybdenum or tungsten, this compound (11) can be represented by the following formula (11-B) or formula (11-C). This compound (11) may be one to which a coordination solvent (e.g., tetrahydrofuran or ethylene elycol dimethyl ether) has further coordinated.

In the case where the metal of the metal catalyst is molybdenum or tungsten, it is preferable that the ligand of the metal catalyst should include an imide ligand ($R^1$—N=M), and examples of $R^1$ include an alkyl group and an aryl group. Also as the ligand [L] of the metal catalyst, a ligand including two coordinating oxygen atoms is preferable. The term "a ligand including two coordinating oxygen atoms" means both cases, that is, the case where a ligand having two of more oxygen atoms coordinates by two of the oxygen atoms thereof and the case where two monodentate ligands each having an oxygen atom coordinate (these monodentate ligands may be the same or different).

[Chem. 9]

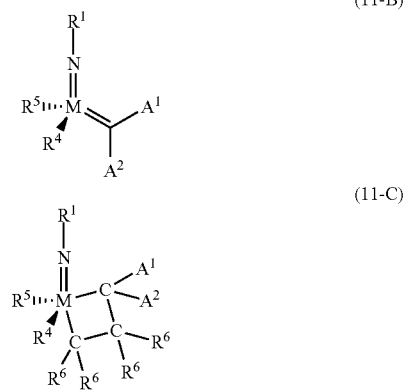

The ligand [L] in the formula (11) is represented by =$NR^1$, —$R^4$, and —$R^5$ in formula the (11-B). The position of the =$NR^1$, —$R^4$, and —$R^5$ is not limited, and may be replaced with each other in the formula (11-B). M is molybdenum or tungsten. Examples of $R^1$ include an alkyl group and an aryl group. Examples of $R^4$ and $R^5$ include a halogen atom, an alkyl group, an aryl group, an alkoxy group, an aryloxy group, a sulfonate group, an amino group (e.g., an alkylamino group, $\eta^1$-pyrrolido, and $\eta^5$-pyrrolido). $R^4$ and $R^5$ may be linked to each other to be a bidentate ligand.

The formula (11-C) is a compound in which an olefin ($C_2(R^6)_4$) has added through cycloaddition ([2+2] cycloaddition) to the metal-carbon doable bond moiety of a compound represented by the formula (11-B) to form a metallacyclobutane ring. The four $R^6$'s respectively are monovalent functional groups which may be the same or different, and examples thereof include a hydrogen atom, a halogen atom, an aryl group, an alkoxy group, an aryloxy group, and an amino group. A compound represented by the formula (11-C) is considered to be equivalent to a compound represented by the formula (11-B).

In formula (11-B) and formula (11-C), $A^1$ and $A^2$ are respectively the same as the $A^1$ and $A^2$ in the formula (11).

The above-mentioned catalyst is generally referred to as a "molybdenum-carbene complex" or "tungsten-carbene complex", and for example, the molybdenum-carbene complexes or tungsten-carbene complexes described in Grela, K. (Ed), *Olefin Metathesis: Theory and Practice*, Wiley, 2014 can be used. Also for example, molybdenum-carbene complexes or tungsten-carbene complexes commercially available from Aldrich Co., Strem Inc., or XiMo AG.

The above-mentioned molybdenum-carbene complexes or tungsten-carbene complexes may be used either singly or in combination of two or more kinds thereof. Further if desired, these may be used as immobilized by a carrier such as silica gel, alumina, polymer or the like.

Specific examples of the compound (11-B) are shown below. Me means a methyl group, i-Pr means an isopropyl group, t-Bu means a tertiary butyl group, and Ph means a phenyl group.

[Chem. 10]

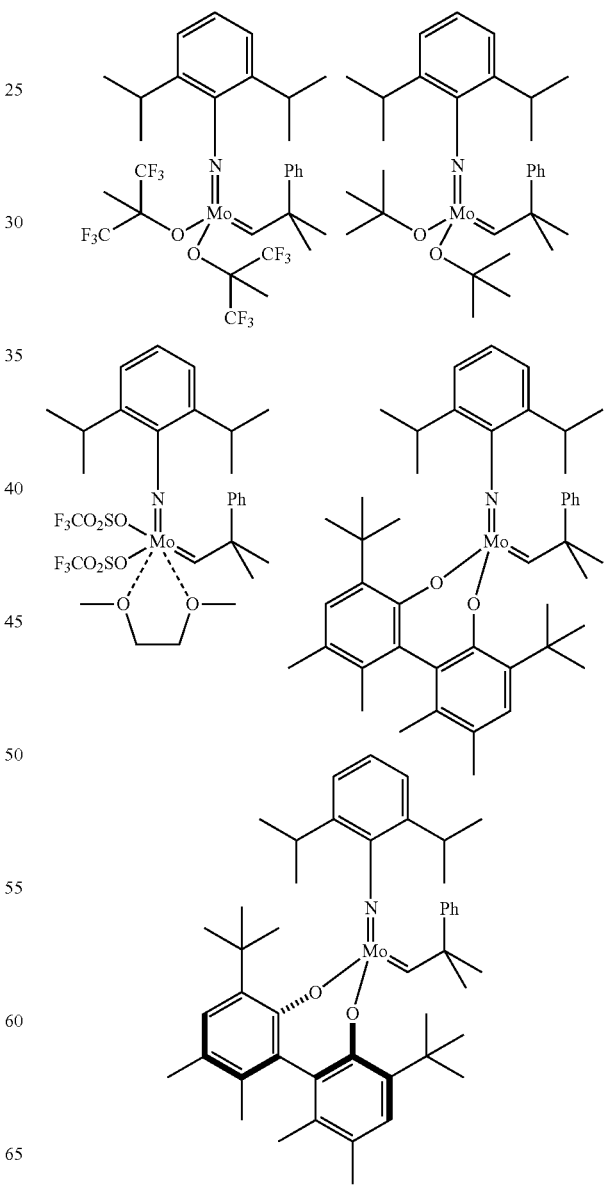

-continued
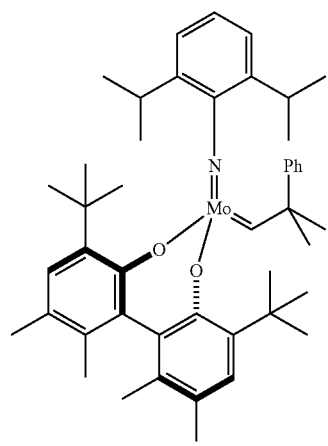
[Chem. 11]
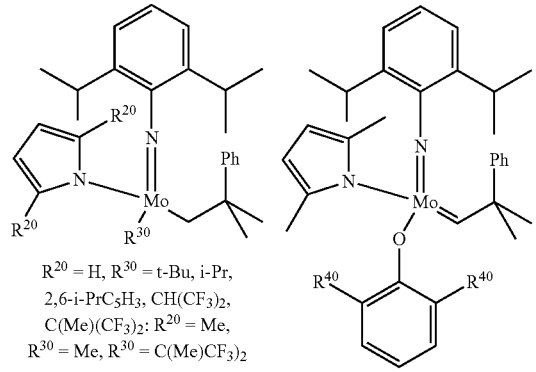
R[20] = H, R[30] = t-Bu, i-Pr,
2,6-i-PrC$_5$H$_3$, CH(CF$_3$)$_2$,
C(Me)(CF$_3$)$_2$; R[20] = Me,
R[30] = Me, R[30] = C(Me)CF$_3$)$_2$
R[40] = 2,4,6-Me$_3$C$_6$H$_2$,
2,4,6-i-Pr$_3$C$_6$H$_2$
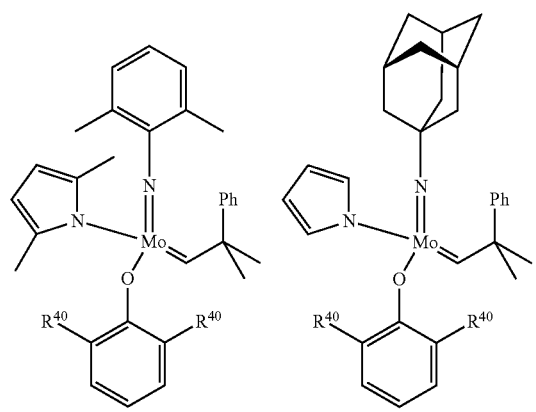
R[40] = 2,4,6-Me$_3$C$_6$H$_2$,
2,4,6-i-Pr$_3$C$_6$H$_2$
R[40] = 2,4,6-Me$_3$C$_6$H$_2$,
2,4,6-i-Pr$_3$C$_6$H$_2$
-continued
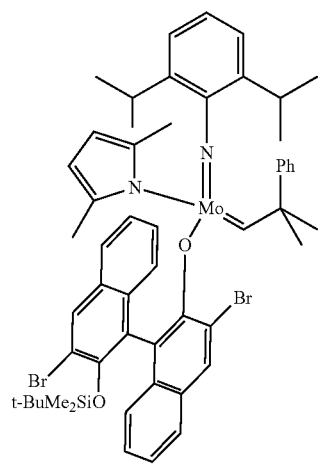
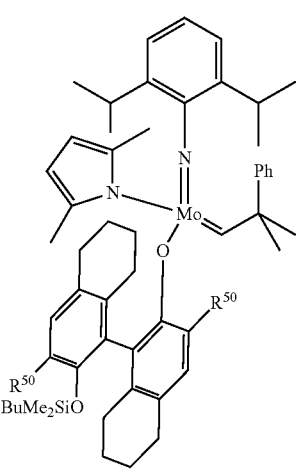
R[50] = Br, Cl
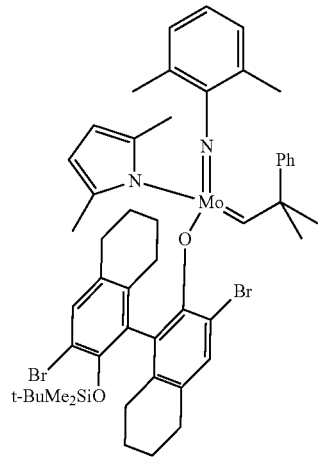

-continued

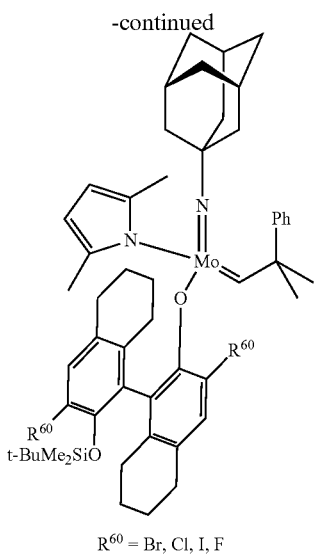

R⁶⁰ = Br, Cl, I, F

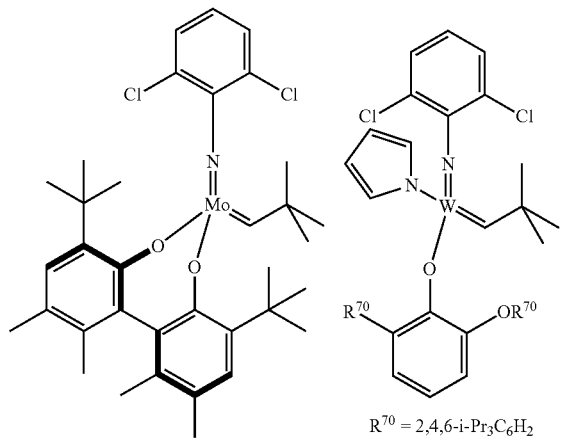

R⁷⁰ = 2,4,6-i-Pr₃C₆H₂

Specific examples of the compound (11-C) include the following compound.

[Chem. 12]

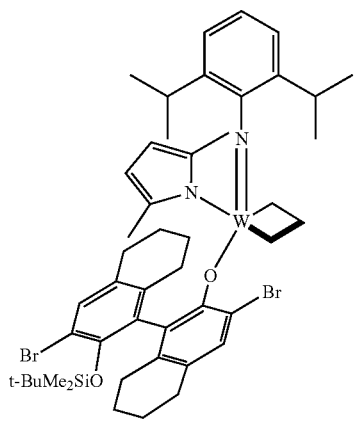

<Compounds (12) to (17)>

Like the compound (11) described above, the compounds (12) to (17) serve as catalysts in the production method according to the present invention and mean both ones charged as a reagent and ones formed during the reaction (catalytically active species).

<Compound (21)>

The olefin compound represented by the following formula (21) is an olefin compound used as a starting material. $X^{11}$, $X^{12}$, and $X^{13}$ in the compound (21) are as defined hereinabove.

[Chem. 13]

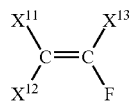

(21)

Namely, $X^{11}$ and $X^{12}$ in the compound (21) are each independently a group selected from the group consisting of a hydrogen atom, a halogen atom, an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, a (per)halogenated aryloxy group having a carbon number of from 5 to 20, and the following groups each further containing one or more atoms selected from the group consisting of an oxygen atom, a nitrogen atom, a sulfur atom, a phosphorus atom, and a silicon atom: an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20. $X^{11}$ and $X^{12}$ may bond, each as a divalent group formed by removing one hydrogen or halogen atom, to each other to form a ring.

Of these, hydrogen and halogen atoms are preferred from the viewpoint of availability.

$X^{13}$ is a group selected from the group consisting of a halogen atom, an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, a (per)halogenated aryloxy group having a carbon number of from 5 to 20, and the following groups each further containing one or more atoms selected from the group consisting of an oxygen atom, a nitrogen atom, a sulfur atom, a phosphorus atom, and a silicon atom: an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20.

Of these, from the viewpoint of availability, $X^{13}$ is preferably a halogen atom or a perhalogenated alkyl group having a carbon number of from 1 to 12, and is more preferably a halogen atom or a perfluorinated alkyl group having a carbon number of from 1 to 8.

It is preferable that the compound (21) should be an olefin compound in which $X^{11}$ is group (i), group (ii), group (v), or group (vi), $X^{12}$ is group (i), group (ii), group (v), or group (vi), and $X^{13}$ is group (ii), group (v), or group (vi). The compound (21) is preferably a 1,1-difluoroolefin or a 1,2-difluoroolefin, more preferably a 1,1-difluoroolefin or a 1,2-difluoroolefin having 3 or more carbon atoms. Especially preferred is a compound in which $X^{13}$ is a fluorine atom, i.e., a 1,1-difluoroolefin.

Preferred examples of compound (21) include, specifically, the following compounds. In the case where there are E/Z isomers, either isomer may be used. As the compound (21), only one kind thereof may be used, or two or more kinds thereof may be used in combination. However, since by-products are prone to be produced in a large amount, it is preferred to use only one kind thereof.

[Chem. 14]

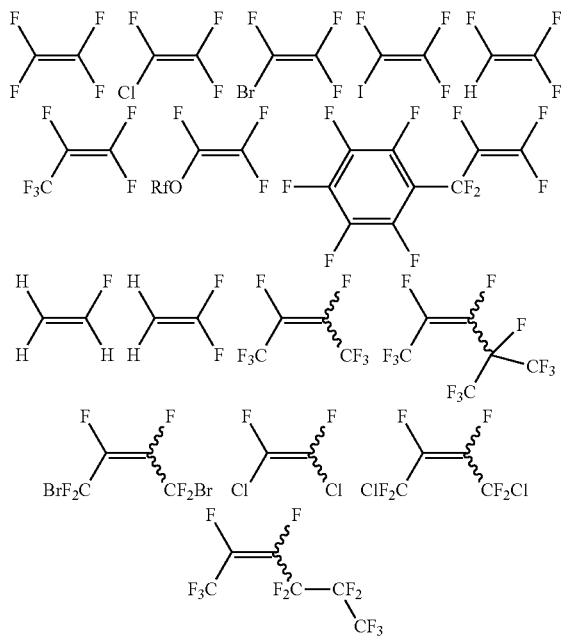

In the formulae, Rf is a (per)fluorinated alkyl group having a carbon number of from 1 to 20, a (per)fluorinated alkyl group having a carbon number of from 1 to 20 and having an etheric oxygen atom between a carbon atom and a carbon atom, or a (per)fluorinated aryl group having a carbon number of from 5 to 20.

More preferred specific examples of the compound (21) include the following compounds.

[Chem. 15]

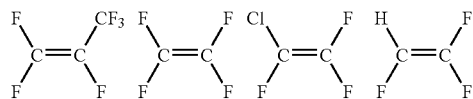

<Compound (31)>

The olefin compound represented by the following formula (31) is a compound used as a starting material. $R^{11}$, $R^{12}$ $R^{13}$ and $R^{14}$ in the compound (31) are as defined hereinabove.

[Chem. 16]

Namely, $R^{11}$ to $R^{14}$ in the compound (31) are each independently a group selected from the group consisting of —H, —CH$_2$R, —CH(CR$_3$)$_2$, —C(CR$_3$)$_3$, and —Ar, wherein the Rs are each independently a group selected from the group consisting of a hydrogen atom, an alkyl group having a carbon number of from 1 to 12, and an alkyl group having a carbon number of from 1 to 12 and having an etheric oxygen atom between carbon atoms, and Ar is an aryl group having a carbon number of from 5 to 12. $R^{11}$ and $R^{12}$ may bond, each as a divalent group formed by removing one hydrogen atom, to each other to form a ring, and $R^{13}$ and $R^{14}$ may bond, each as a divalent group formed by removing one hydrogen atom, to each other to form a ring.

Preferred of these are —H and —CH$_2$R since these compounds have a high reactivity.

More preferred specific examples of the compound (31) include ethylene, propylene, 1-butene, isobutene, styrene, and the like.

<Compounds (41) and (42)>

The olefin compound represented by the following formula (41) or the following formula (42) is a compound which is used like a catalyst in the metathesis reaction in the present invention. $A^{11}$, $A^{12}$, $A^{13}$, and E in the olefin compound (41) and the olefin compound (42) are as defined hereinabove.

[Chem. 17]

Namely, $A^{11}$ and $A^{12}$ in the compound (41) and $A^{11}$ in the compound (42) are each independently a group selected from the group consisting of a hydrogen atom, a chlorine atom, a bromine atom, an iodine atom, a monovalent hydrocarbon group having a carbon number of from 1 to 20, and a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom. In the compound (41), $A^{11}$ and $A^{12}$ may bond, each as a divalent group formed by removing one hydrogen or halogen atom, to each other to form a ring. In the case where one of $A^{11}$ or $A^{12}$ is a halogen atom, the case where the other is a halogen atom is excluded.

Preferred of these is the case where at least one of $A^{11}$ or $A^{12}$ is a hydrogen atom since these compounds have a high reactivity.

In the case where at least one of $A^{11}$ or $A^{12}$ has a plurality of R's in one molecule, as represented by —OSiR'$_3$ or —NR'$_2$, the total number of carbon atoms of the plural R's is the range of the number of carbon atoms of the $A^{11}$ and/or $A^{12}$.

$A^{13}$ is a group selected from the group consisting of a hydrogen atom, a monovalent hydrocarbon group having a carbon number of from 1 to 20, and a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom.

E is a group selected from the group consisting of —OR', —OSiR'$_3$, —NR'$_2$, —SR', and group (iia). The R's are each independently a group selected from the group consisting of group (i): a hydrogen atom, group (v): a group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20 and group (vi): the group (v) further containing one or more atoms selected from the group consisting of an oxygen atom, a nitrogen atom, a sulfur atom, a phosphorus atom, and a silicon atom. In the case of —NR'$_2$, the two R's may bond, each as a divalent group formed by removing one hydrogen atom, to each other to form a ring.

$A^{13}$ and E may bond, each as a divalent group formed by removing one hydrogen or halogen atom, to each other to form a ring. In the olefin compound (42), $A^{11}$ and E may bond, each as a divalent group formed by removing one hydrogen or halogen atom, to each other to form a ring.

It is preferable that two or three of $A^{11}$ to $A^{13}$ should be hydrogen atoms. It is especially preferable that $A^{13}$ should be a hydrogen atom since these compounds have a high reactivity.

It is preferable that E should be —OR', —NR'$_2$, or —SR' from the viewpoint that these compound have a high reactivity. Namely, the compound (41) preferably is vinyl ethers, vinyl esters, vinyl amines, or vinyl thioethers, from the viewpoint that these compounds have a high reactivity. The compound (42) preferably is a 1,2-bisalkoxyethylenes, 1,2-bisacyloxyethylenes, 1,2-bisaminoethylenes, or 1,2-bisthioalkoxyethylenes, from the viewpoint that these compounds have a high reactivity.

More preferred specific examples of the compound (41) and the compound (42) include the compounds shown below.

[Chem. 18]

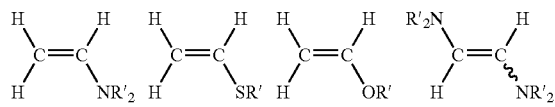

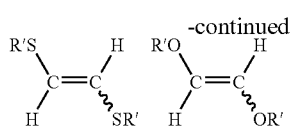

Even more preferred examples include the compounds shown below.

[Chem. 19]

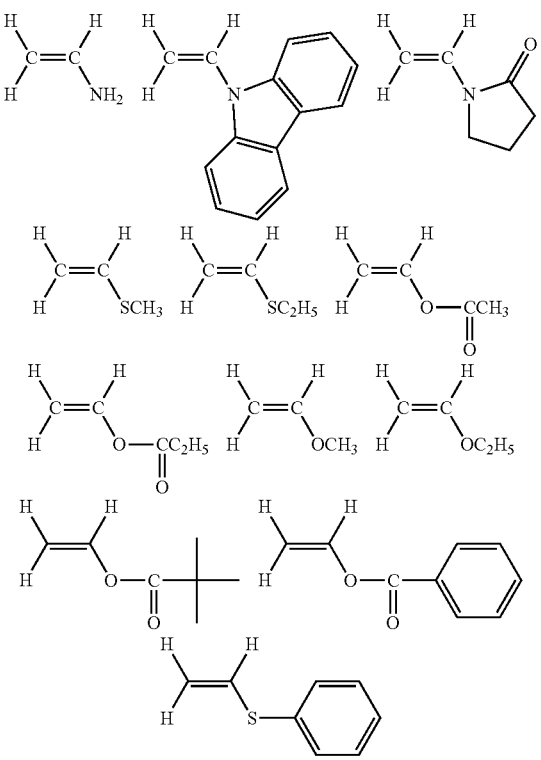

<Compound (51) and Compound (52)>

Through the reaction between the compound (21) and the compound (31) described above, at least one of a fluorine-containing olefin compound represented by the following formula (51) or a fluorine-containing olefin compound represented by the following formula (52) is produced. $R^{11}$, $R^{12}$, $R^{13}$, $R^{14}$, and $X^{13}$ in the compound (51) and the compound (52) are as defined hereinabove, and preferred examples of these are also respectively the same as those of the $R^{11}$, $R^{12}$, $R^{13}$, $R^{14}$, and $X^{13}$ and contained in the compound (21) or the compound (22).

The compound (51) and/or the compound (52) is a fluorine-containing olefin compound in which a fluorine atom has directly bonded to one of carbon atoms constituting a carbon-carbon double bond.

There are cases where the reaction between the compound (21) and the compound (31) forms an olefin compound represented by the following formula (53) or an olefin compound represented by the following formula (54). However, an explanation on the compound (53) and the compound (54) is omitted because the present invention is intended to produce at least one fluorine-containing olefin compound of the compound (51) or the compound (52).

[Chem. 20]

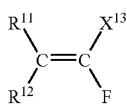
(51)

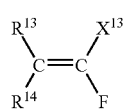
(52)

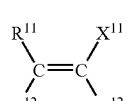
(53)

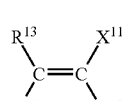
(54)

Compound (51) and/or compound (52) is obtained, for example, by selecting hexafluoropropylene, tetrafluoroethylene, chlorotrifluoroethylene, or trifluoroethylene as compound (21) and ethylene, propylene, 1-butene, isobuteue, or styrene as compound (31) and reacting the selected compounds.

Preferred specific examples of compound (51) and/or compound (52) include the compounds shown below.

[Chem. 21]

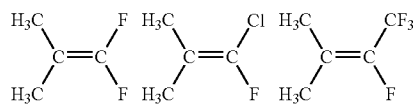

<Production Method>

The present invention relates to a method for producing a fluorine-containing olefin compound through olefin metathesis. Typically, a fluorine-containing olefin (a compound (21)) and another olefin (a compound (31)) are used as starting-material compounds, and the starting-material compounds are brought into contact with each other in the presence of a metal-carbene complex compound (10) and an olefin (a compound (41) or a compound (42)) different from the starting-material compounds, thereby performing an olefin metathesis to obtain new a fluorine-containing olefin (a compound (51) and/or a compound (52)) having partial structures of the two kinds of starting-material compounds.

The compound (21) and the compound (31) to be used as starting-material compounds each can be either a terminal olefin or an internal olefin. From the viewpoint of improving the yield of the desired product, it is preferable that the starting-material compounds to be used should be ones which have been degassed and dried. Although there are no particular limitations on degassing operations, there are cases where freeze-pump-thaw degasification or the like is carried out. Although there are no particular limitations on drying operations, the compounds are usually brought into contact with a molecular sieve or the like. Usually, the degassing and drying operation for the starting-material compounds are conducted before they are brought into contact with a metal-carbene complex compound (10) and/or a compound (41) (or a compound (42)).

There are cases where the olefins to be used as starting materials contain a slight amount of impurities (e.g., peroxides, etc.). The olefins may hence be purified from the viewpoint of improving the desired product yield. There are no particular limitations on purification methods. For example, the olefins can be purified in accordance with a method described in a document (Armarego, W. L. F. et al, Purification of Laboratory Chemicals (Sixth Edition), 2009, Elsevier).

The compound (21) and the compound (31) as starting-material compounds may be mixed together beforehand and put into a reactor or may be put thereinto separately. There are cases where as a starting-material compound, the compound (21) or the compound (31) is brought into contact with a metal-carbene complex compound and/or the compound (41) (or the compound (42)) and then the other starting-material compound is brought into contact with the resultant mixture.

There are no particular limitations on the molar ratio between compound (21) and compound (31) as starting materials. Usually, based on one mol of one basis olefin compound, the other acetylene is used in an amount of from 0.01 to 100 mol or so, and preferably from 0.1 to 10 mol or so.

The metal-carbene complex compound may be put into as a reagent or may be generated in the system.

In the case where it is put into as a reagent, a commercially-available metal-carbene complex may be used directly as it is, or a commercially-unavailable metal-carbene complex synthesized from a commercially-available reagent according to a known method may be used.

In the case where it is generated in the system, a metal-carbene complex prepared from a metal complex as a precursor according to a known method may be used in the present invention.

The amount of the metal-carbene complex, compound to be used is not particularly limited. Usually, it is used from 0.0001 to 1 mol or so, and preferably from 0.001 to 0.2 mol or so, based on one mol of one basis olefin compound.

The metal-carbene complex compound to be used is usually put into the reactor as it is solid, but may be put thereinto after dissolved or suspended in a solvent. The solvent to be used here is not particularly limited within a range not having any negative influence on the reaction. An organic solvent, a fluorine-containing organic solvent, an ionic liquid, water, and the like can be used either singly or in combination thereof. Of these solvent molecules, a part or all of the hydrogen atoms may be substituted with deuterium atoms.

The compound (41) (or the compound (42)) is put into as a reagent. However, after the compound (41) is put into once, a compound (corresponding to a compound (41)' in Scheme (a) described hereinabove) generated therefrom invite system also contributes to the olefin metathesis reaction. As the compound (41) (or the compound (42)), a commercially-available compound may be used directly as it is, or a commercially-unavailable compound synthesized from a commercially-available reagent according to a known method may be used.

The amount of compound (41) (or compound (42)) to be used is not particularly limited. Usually, it is used from 0.0001 to 1 mol or so, and preferably from 0.001 to 0.2 mol or so, based on one mol of one basis olefin compound.

The compound (41) (or the compound (42)) to be used is usually put into the reactor as it is liquid or solid, but may be put thereinto after dissolved or suspended in a solvent. The solvent to be used here is not particularly limited within a range not having any negative influence on the reaction. An organic solvent, a fluorine-containing organic solvent, an ionic liquid, water, and the like can be used either singly or in combination thereof. Of these solvent molecules, a part or all of the hydrogen atoms may be substituted with deuterium atoms.

In the case where the olefin compound is liquid (including the case where the compound liquefies upon heating), it is preferred not to use solvent in the metathesis reaction. In this case, it is preferable that the metal-carbene complex compound should dissolve in the olefin compound.

As the organic solvent, usable are an aromatic hydrocarbon solvent such as benzene, toluene, o-, m- or p-xylene, mesitylene, or the like; an aliphatic hydrocarbon solvent such as hexane, cyclohexane or the like; a halogen-containing solvent such as dichloromethane, chloroform, 1,2-dichloroethane, chlorobenzene, o-dichlorobenzene, or the like; and an ether solvent such as tetrahydrofuran, dioxane, diethyl ether, glyme, diglyme, or the like; and the like. As the fluorine-containing organic solvent, for example, usable are hexafluorobenzene, m-bis(trifluoromethyl)benzene, p-bis(trifluoromethyl)benzene, α,α,α-trifluoromethylbenzene, dichloropentafluoropropan, and the like. As the ionic liquid, for example, usable are various pyridinium salts, various imidazolium salts and the like. Of the above-mentioned solvents, benzene, toluene, o-, m-, and p-xylenes, mesitylene, dichloromethane, chloroform, chlorobenzene, o-dichlorobenzene, diethyl ether, dioxane, THF (tetrahydrofuran), hexafluorobenzene, m-bis(trifluoromethyl)benzene, p-bis(trifluoromethyl)benzene, α,α,α-trifluoromethylbenzene, and mixtures thereof are preferred from the view point of the solubility therein of the metal-carbene complex, or the like.

From the viewpoint of improving the yield of the desired product, it is preferable that the starting-material compounds to be used should be ones which have been degassed and dried. Although there are no particular limitations on degassing operations, there are cases where freeze-pump-thaw degasification or the like is carried out. Although there are no particular limitations on drying operations, the compounds are usually brought into contact with a molecular sieve or the like. Usually, the degassing and drying operation are conducted before they are brought into contact with a metal-carbene complex compound.

The atmosphere in which the starting-material compounds are brought into contact with the metal-carbene complex compound is not particularly limited. From the viewpoint of prolonging the catalyst life, inert gas atmosphere is preferred. In particular, a nitrogen or argon atmosphere is preferred. However, in the case where compounds which are gaseous under reaction conditions are used as starting materials, the gaseous atmosphere of these can be employed.

The phase in which the starting-material compounds are brought into contact with the metal-carbene complex compound and/or the compound (41) (or the compound (42)) is not particularly limited. From the viewpoint of reaction rate, a liquid phase is usually, employed, in the case where the compounds as starting materials are gaseous under the reaction conditions, it is difficult to carry out in a liquid phase, and hence can be carried out in a gaseous-liquid two-phase system. In the case of carrying out in a liquid phase, a solvent can be used. As the solvent, use can be made of the same solvent as that used for dissolving or suspending the metal-cubene complex compound and/or the compound (41) (or the compound (42)). In the case where at least one of the two starting-material compounds is liquid under the reaction conditions, the reaction can be carried out without any solvent.

The container in which the starting-material compounds are brought into contact with the metal-carbene complex compound is not particularly limited within a range not having any negative influence on the reaction. For example, use can be made of a metal container, a glass container, or the like. Since there are cases where the olefin metathesis according to the present invention involves handling of an olefin compound which is in a gaseous state under the reaction conditions, a pressure-proof container capable of being highly gas-tightly sealed is preferred.

The temperature at which the starting-material compounds are brought into contact with the metal-carbene complex compound is not particularly limited. Usually, it may be carried out at a temperature in a range of from −100 to 200° C. From the viewpoint of reaction rate, it is preferably from 0 to 150° C. Since there are cases where the reaction does not start at low temperatures and where the complex decomposes rapidly at high temperatures, it is necessary to suitably set a lower limit and an upper limit of temperatures. Usually, the reaction may be carried out at a temperature not higher than the boiling point of the solvent used.

The time for which the starting-material compounds are brought into contact with the metal-carbene complex compound is not particularly limited. The reaction is carried out usually in a range of 1 minute to 48 hours.

The pressure under which the starting-material compounds are brought into contact with the metal-carbene complex compound is not particularly limited. The pressure may be either an increased pressure or ordinary pressure or a reduced pressure. It is usually from 0.001 to 10 MPa or so, preferably from 0.01 to 1 MPa or so.

An inorganic salt, an organic compound, a metal complex, or the like may be made to coexist when bringing the starting-material compounds into contact with the metal-carbene complex compound, within a range not having any negative influence on the reaction.

Furthermore, the mixture of the starting-material compounds with the metal-carbene complex compound and/or the compound (41) (or the compound (42)) may be stirred within a range not having any negative influence on the reaction. In stirring method in this case, use can be made of a mechanical stirrer, magnetic stirrer, or the like.

After the starting-material compounds are brought into contact with the metal-carbene complex compound and/or the compound (41) (or the compound (42)), the products are obtained usually as a mixture of a plurality of fluorine-containing olefins, and may hence be isolated by a known method. Examples of isolation methods include distillation, column chromatography, recycling preparative HPLC, and the like. If desired, these may be employed either singly or in combination of plural kinds thereof.

The desired products obtained by this reaction can be identified according to a known method that is the same as a method for ordinary organic compounds. Examples, thereof include $^1$H—, $^{19}$F—, or $^{13}$C-NMR, GC-MS, and the like. If desired, these may be employed either singly or in combination of plural kinds thereof.

EXAMPLES

The present invention is explained below in detail by reference to Examples, but the invention should not be construed as being limited thereto.

<Commercial Reagents>

In the Examples, as for the catalyst, commercial products were used in the reaction directly as they are, unless otherwise specifically indicated. As for solvents (benzene-$d_6$ and o-dichlorobenzene-$d_4$), commercial products were previously degassed by freeze-pump-thaw cycles and subsequently dried with Molecular Sieve 4A and were then used in the reaction.

<Evaluation Methods>

The structure of the compound synthesized in the Examples was identified through measurement of $^1$H-NMR and $^{19}$F-NMR spectroscopy with a nuclear magnetic resonance spectroscope (JNM-AL300) manufactured by JEOL Ltd. The molecular weight was measured according to an electron ionization (EI) using a gas chromatography mass s spectrometer (GCMS-QP2010Ultra) manufactured by Shimadzu.

Example 1

Metathesis of Propylene and Tetrafluoroethylene with Grubbs' Second-Generation Catalyst in the Presence of Ethyl Vinyl Ether.

In a nitrogen atmosphere, Grubbs' second-generation catalyst shown below (Grubbs $2^{nd}$, 20 mol %, 0.024 mmol), ethyl vinyl ether (20 mol %, 0.024 mmol), and benzene-$d_6$ (0.6 mL) were weighed and put into a pressure proof NMR tube. Thereafter, the gas-phase part in the NMR tube was replaced with a propylene/tetrafluoroethylene=1/1 mixed gas (v/v, 1.0 atm, 2.7 mL, 0.12 mmol).

The NMR tube was heated at 60° C., and the reaction was conducted at that temperature for 1 hour. After completion of the reaction, NMR of the liquid content was measured to confirm the formation of 1,1-difluoro-1-propene.

The series of reactions is shown below.

[Chem. 22]

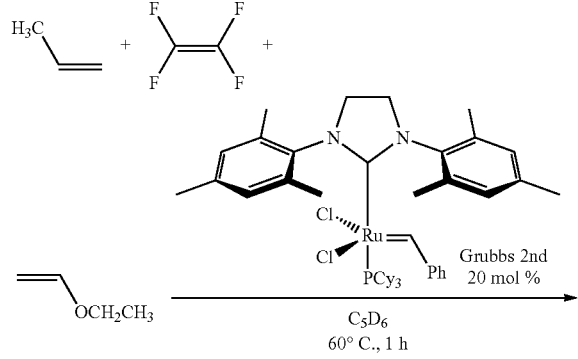

Example 2

Metathesis of Styrene and Tetrafluoroethylene with Grubbs' Second-Generation Catalyst in the Presence of Ethyl Vinyl Ether In a nitrogen atmosphere, styrene (0.12 mmol), Grubbs' second-generation catalyst shown below (Grubbs $2^{nd}$, 20 mol %, 0.024 mmol), ethyl vinyl ether (20 mol %, 0.024 mmol), and o-dichlorobenzene-$d_4$ (0.6 mL) are weighed and put into a pressure-proof NMR tube. Thereafter, the gas-phase part in the NMR tube is replaced with tetrafluoroethylene (1.0 atm, 2.7 mL, 0.12 mmol).

The NMR tube is heated at 180° C., and the reaction is conducted at that temperature for 1 hour. After completion of the reaction, NMR of the liquid content is measured to confirm the formation of β,β-difluorostyrene.

The series of reactions is shown below.

[Chem. 23]

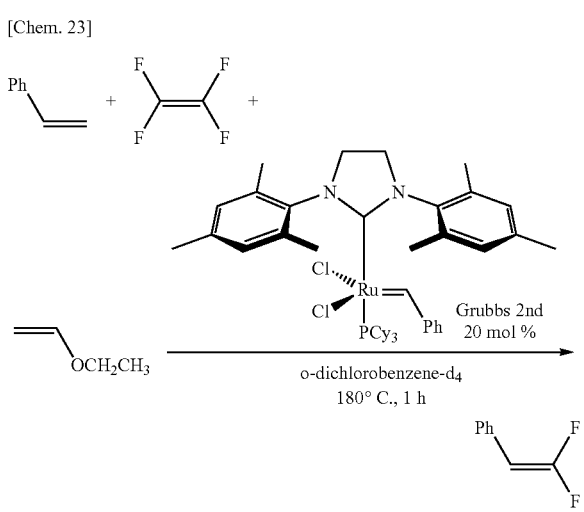

Example 3

Metathesis of Propylene and Tetrafluoroethylene with Grubbs' Second-Generation Catalyst in the Presence of Ethyl Vinyl Ether In a nitrogen atmosphere, Grubbs' second-generation catalyst shown below (Grubbs $2^{nd}$, 20 mol %, 0.024 mmol), ethyl vinyl ether (20 mol %; 0.024 mmol), and benzene-$d_6$ (0.6 mL) are weighed and put into a pressure-proof NMR tube. Thereafter, propylene (1.0 atm; 1.35 mL; 0.06 mmol) is put into the gas-phase part in the NMR tube. The NMR tube is heated at 60° C., and the reaction is conducted at that temperature for 1 hour. Thereafter, tetrafluoroethylene (1.0 atm, 1.35 mL, 0.06 mmol) is put into the gas-phase part in the NMR tube, and further the NMR tube is heated at 60° C. to conduct the reaction at that temperature for 1 hour. After completion of the reaction, NMR of the liquid content is measured to confirm the formation of 1,1-difluoro-1-propene.

The series of reactions is shown below.

[Chem. 24]

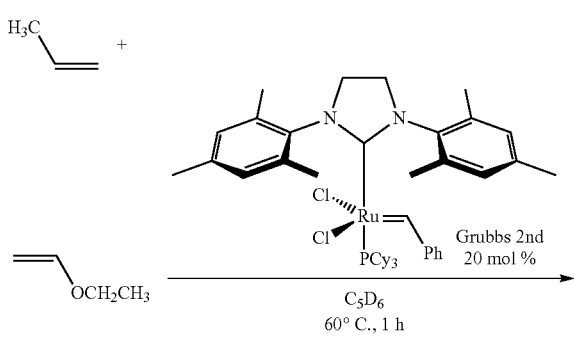

-continued

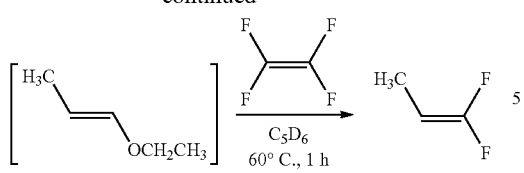

Examples 4 and 5

Metathesis of Propylene and Tetrafluoroethylene with Ruthenium Catalyst in the Presence of Ethyl Vinyl Ether The Grubbs' second-generation catalyst in Example 1 is replaced with the known ruthenium catalysts B and C represented by the following known formulae, and reaction is conducted in the same manner to obtain the same product as in Example 1.

TABLE 1

| Ex. | Catalyst | Structure |
|---|---|---|
| 4 | B | Umicore M51 |
| 5 | C | Umicore M73SIPr |

Examples 6 to 9

Metathesis of Propylene and Tetrafluoroethylene with Ruthenium Catalyst in the Presence of Ethyl Vinyl Ether The Grubbs' second-generation catalyst in Example 1 is replaced with the known molybdenum catalysts D to G represented by the following formulae, and reaction is conducted in the same manner to obtain the same product as in Example 1.

TABLE 2

| Ex. | Catalyst | Structure |
|---|---|---|
| 6 | D | 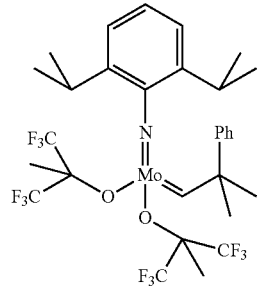 |
| 7 | E | 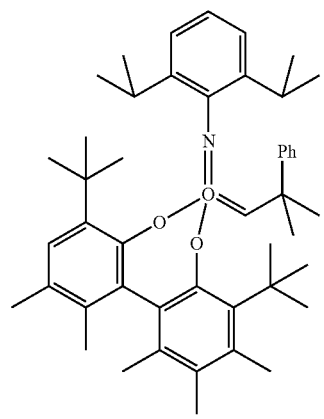 |
| 8 | F | 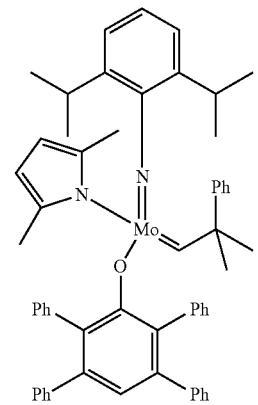 |

TABLE 2-continued

| Ex. | Catalyst | Structure |
|---|---|---|
| 9 | G | (structure: Mo complex with 2,6-diisopropylphenyl imido, 2,5-dimethylpyrrolyl, neopentylidene Ph, and 3,3'-dibromo-2'-(t-BuMe₂SiO)-BINOL-type aryloxide) |

Example 10

Metathesis of Propylene and Tetrafluoroethylene with Tungsten Catalyst in the Presence of Ethyl Vinyl Ether The Grubbs' second-generation catalyst in Example 1 is replaced with the known tungsten catalyst H represented by the following formula, and reaction is conducted in the same manner to obtain the same product as in Example 1.

TABLE 3

| Ex. | Catalyst | Structure |
|---|---|---|
| 10 | H | (structure: W complex with 2,6-diisopropylphenyl imido, 2,5-dimethylpyrrolyl, ethylidene, and 3,3'-dibromo-2'-(t-BuMe₂SiO)-octahydroBINOL-type aryloxide) |

Examples 11 and 12

Metathesis of Styrene and Tetrafluoroethylene with Ruthenium Catalyst in the Presence of Ethyl Vinyl Ether The Grubbs' second-generation catalyst in Example 2 is replaced with the known ruthenium catalysts B and C described above, and reaction is conducted in the same manner to obtain the same product as in Example 2.

Examples 13 to 16

Metathesis of Styrene and Tetrafluoroethylene with Molybdenum Catalyst in the Presence of Ethyl Vinyl Ether The Grubbs' second-generation catalyst in Example 2 is replaced with the known molybdenum catalysts D to G described above, and reaction is conducted in the same manner to obtain the same product as in Example 2.

Examples 17 to 24

Metathesis of Propylene and Tetrafluoroethylene with Ruthenium Catalyst in the Presence of Compound (41)

The ethyl vinyl ether in Example 1 is replaced with the commercial compound (41) represented by the following formulae, and reaction is conducted in the same manner to obtain the same product as in Example 1.

TABLE 4

| Ex. | Compound (41) |
|---|---|
| 17 | $CH_2=CH\text{-}O(CH_2)_3CH_3$ |
| 18 | $CH_2=CH\text{-}O(CH_2)_{11}CH_3$ |
| 19 | $CH_2=CH\text{-}OCH_2CH(CH_2CH_3)(CH_2)_3CH_3$ |
| 20 | $CH_2=CH\text{-}OC(=O)CH_3$ (vinyl acetate) |
| 21 | $CH_2=CH\text{-}N$(2-pyrrolidinone) (N-vinylpyrrolidone) |
| 22 | $CH_2=CH\text{-}N$(carbazole) (N-vinylcarbazole) |
| 23 | $CH_2=CH\text{-}S\text{-}CH_2CH_3$ (ethyl vinyl sulfide) |

TABLE 4-continued

| Ex. | Compound (41) |
|---|---|
| 24 | H₂C=CH-SPh |

Examples 25 to 28

Metathesis of Propylene and Compound (21) with Grubbs' Second-Generation Catalyst in the Presence of Ethyl Vinyl Ether The tetrafluoroethylene in Example 1 is replaced with the compound (21) represented by the following formulae, and reaction is conducted in the same manner. The fluorine-containing olefin compounds shown in Table 5 are obtained as products.

TABLE 5

| Ex. | Compound (21) | Fluorine-containing olefin compound (21) |
|---|---|---|
| 25 | CFCl=CF₂ | CH₃-CF=CF₂, CH₃-CF=CFCl |
| 26 | CHF=CF₂ | CH₃-CF=CF₂, CH₃-CF=CHF |
| 27 | CFCl=CFCl | CH₃-CF=CFCl |
| 28 | CF₃-CF=CF₂ | CH₃-CF=CF₂, CH₃-CF=CFCF₃ |

Example 29

Metathesis of Propylene and Tetrafluoroethylene with Grubbs' Second-Generation Catalyst in the Presence of Ethyl Vinyl Ether Using No Solvent In Example 1, the solvent (benzene-d₆) is not put, and reaction is conducted in the same manner. Thus, the same product as in Example 1 is obtained.

Example 30

Metathesis of Styrene and Tetrafluoroethylene with Grubbs' Second-Generation Catalyst in the Presence of Ethyl Vinyl Ether Using No Solvent In Example 2, the solvent (benzene-d₆) is not put, and reaction is conducted in the same manner. Thus, the same product as in Example 2 is obtained.

Comparative Example 1

Metathesis of Propylene and Tetrafluoroethylene with Grubbs' Second-Generation Catalyst in the Absence of Ethyl Vinyl Ether In a nitrogen atmosphere, Grubbs' second-generation catalyst shown below (Grubbs 2nd; 20 mol %, 0.024 mmol) and benzene-d₆ (0.6 mL) were weighed and put into a pressure-proof NMR tube. Thereafter, the gas-phase part in the NMR tube was replaced with a propylene/tetrafluoroethylene=1/1 mixed gas (v/v, 1.0 atm, 2.7 mL, 0.12 mmol).

The NMR tube was heated at 60° C., and the reaction was conducted at that temperature for 1 hour. After completion of the reaction, NMR of the liquid content is measured. However, 1,1-difluoro-1-propene was formed only in a trace amount.

The series of reactions is shown below.

[Chem. 25]

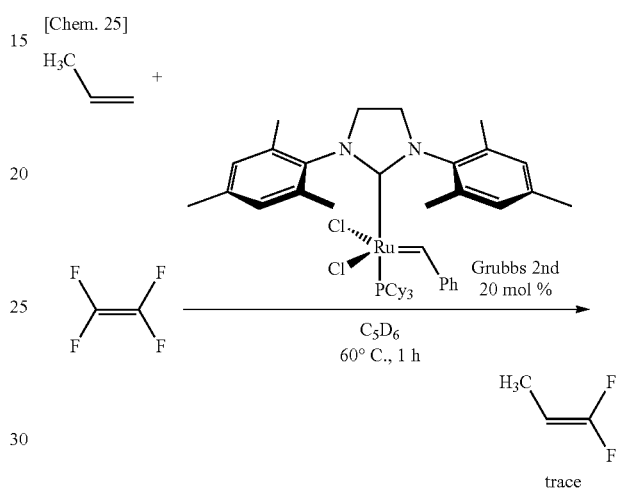

Comparative Example 2

Metathesis of Styrene and Tetrafluoroethylene with Grubbs' Second-Generation Catalyst in the Absence of Ethyl Vinyl Ether In a nitrogen atmosphere, styrene (0.12 mmol), Grubbs' second-generation catalyst shown below (Grubbs 2ⁿᵈ, 20 mol %, 0.024 mmol), and o-dichlorobenzene-d₄ (0.6 mL) are weighed and put into a pressure-proof NMR tube. Thereafter, the gas-phase part in the NMR tube is replaced with tetrafluoroethylene (1.0 atm, 2.7 mL, 0.12 mmol).

The NMR tube is heated at 180° C., and the reaction is conducted at that temperature for 1 hour. After completion of the reaction, NMR of the liquid content is measured to confirm that β,β-difluorostyrene is generated only in a trace amount or is not formed at all.

The series of reactions is shown below.

[Chem. 26]

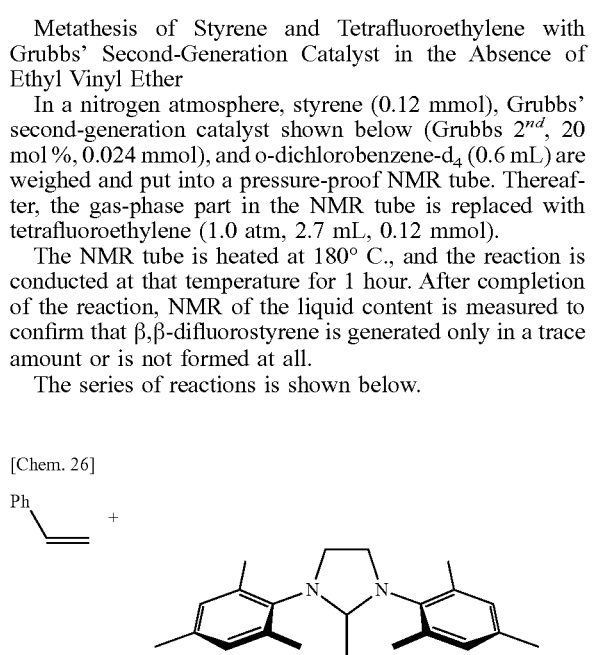

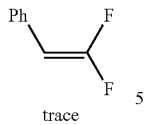

trace

While the invention has been described in detail and with reference to specific embodiments thereof, it will be apparent to one skilled in the art that various changes and modifications can be made therein without departing from the spirit and scope thereof. This application is based on a Japanese patent application filed on Mar. 3, 2015 (Application No. 2015-041644), the contents thereof being incorporated herein by reference.

INDUSTRIAL APPLICABILITY

According to the present invention, a fluorine-containing olefin compound can be easily and highly efficiently produced by carrying out a metathesis reaction of a fluorine-containing olefin and another olefin in the presence of a metal-carbene complex compound and a third olefin compound.

The invention claimed is:

1. A method for producing at least one compound of a fluorine-containing olefin compound of formula (51) or a fluorine-containing olefin compound of formula (52), the method comprising:
reacting a fluorine-containing olefin compound of formula (21) with an olefin compound of formula (31) to form the fluorine-containing olefin compound of formula (51) or the fluorine-containing olefin compound of formula (52);
wherein the reaction is carried out in the presence of a metal-carbene complex compound (10) having an olefin metathesis reaction activity and a compound of formula (41), or in the presence of the metal-carbene complex compound (10) and an olefin compound of formula (42):

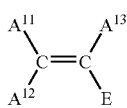
(41)

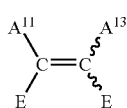
(42)

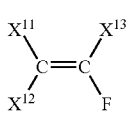
(21)

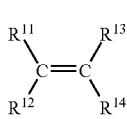
(31)

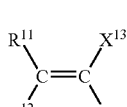
(51)

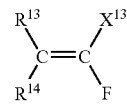
(52)

wherein $A^{11}$ and $A^{12}$ are each independently a group selected from the group consisting of group (i), group (iia), group (iii), and group (iv), and $A^{11}$ and $A^{12}$ may bond to each other to form a ring;
with the proviso that in the case where one of $A^{11}$ or $A^{12}$ is a halogen atom, the other is a group selected from the group consisting of group (i), group (iii), and group (iv);
$A^{13}$ is a group selected from the group consisting of the following group (i), group (iii), and group (iv);
E is a group selected from the group consisting of —OR', —OSiR'$_3$, —NR'$_2$, —SR', and group (iia), and each R' is independently a group selected from the group consisting of group (i), group (v), and group (vi);
$A^{13}$ and E may bond to each other to form a ring;
$X^{11}$ and $X^{12}$ are each independently a group selected from the group consisting of group (i), group (ii), group (v), and group (vi), and $X^{11}$ and $X^{12}$ may bond to each other to form a ring;
$X^{13}$ is a group selected from the group consisting of group (ii), group (v), and group (vi);
$R^{11}$ to $R^{14}$ are each independently a group selected from the group consisting of —H, —CH$_2$R, —CH(CR$_3$)$_2$, —C(CR$_3$)$_3$, and —Ar,
wherein each R is independently a group selected from the group consisting of a hydrogen atom, an alkyl group having a carbon number of from 1 to 12, and an alkyl group having a carbon number of from 1 to 12 and having an etheric oxygen atom between carbon atoms, and Ar is an aryl group having a carbon number of from 5 to 12;
$R^{11}$ and $R^{12}$ may bond to each other to form a ring;
$R^{13}$ and $R^{14}$ may bond to each other to form a ring;
group (i): a hydrogen atom;
group (ii): a halogen atom;
group (iia): a chlorine atom, a bromine atom, or an iodine atom;
group (iii): a monovalent hydrocarbon group having a carbon number of from 1 to 20;
group (iv): a monovalent hydrocarbon group having a carbon number of from 1 to 20 and containing one or more atoms selected from the group consisting of a halogen atom, an oxygen atom, a nitrogen atom, a sulfur atom, a phosphorus atom, and a silicon atom;
group (v): a group selected from the group consisting of an alkyl group having a carbon number of from 1 to 12, an alkoxy group having a carbon number of from 1 to 12, an aryl group having a carbon number of from 5 to 20, an aryloxy group having a carbon number of from 5 to 20, a (per)halogenated alkyl group having a carbon number of from 1 to 12, a (per)halogenated alkoxy group having a carbon number of from 1 to 12, a (per)halogenated aryl group having a carbon number of from 5 to 20, and a (per)halogenated aryloxy group having a carbon number of from 5 to 20;
group (vi): the group (v) further containing one or more atoms selected from the group consisting of an oxygen atom, a nitrogen atom, a sulfur atom, a phosphorus atom, and a silicon atom.

2. The production method according to claim 1, wherein the olefin compound of formula (41) or formula (42) is at least one compound selected from the group consisting of

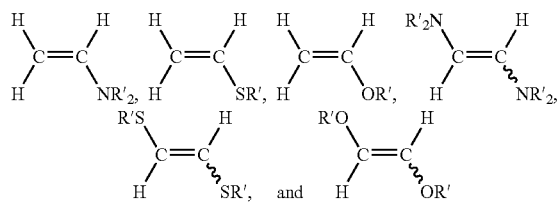

wherein each R' is independently a group selected from the group consisting of group (i), group (v), and group (vi).

3. The production method according to claim 1, wherein $X^{13}$ in the fluorine-containing olefin compound of formula (21) is a halogen atom or a perhalogenated alkyl group having a carbon number of from 1 to 8.

4. The production method according to claim 1, wherein a metal in the metal-carbene complex compound (10) is ruthenium, molybdenum, or tungsten.

5. The production method according to claim 1, wherein a metal in the metal-carbene complex compound (10) is ruthenium.

6. The production method according to claim 1, wherein a metal in the metal-carbene complex compound (10) is molybdenum or tungsten and the metal-carbene complex compound (10) has an imide ligand and a ligand including two coordinating oxygen atoms as a ligand [L].

7. The production method according to claim 1, wherein in the olefin compound of formula (21), $X^{11}$ is group (i), group (ii), group (v), or group (vi), $X^{12}$ is group (i), group (ii), group (v), or group (vi), and $X^{13}$ is group (ii), group (v) or group (vi).

8. The production method according to claim 1, wherein the olefin compound of formula (21) is a 1,1-difluoroolefin.

9. The production method according to claim 1, wherein the olefin compound of formula (21) is at least one olefin compound selected from the group consisting of

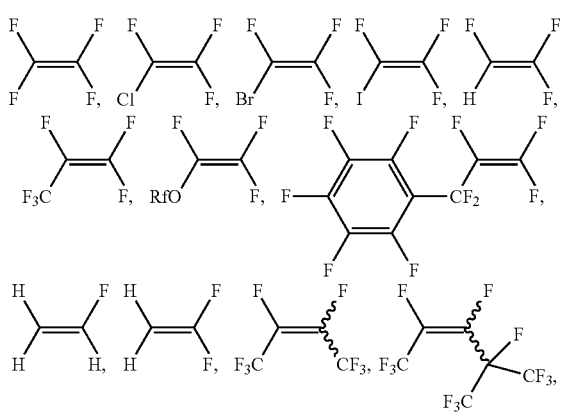

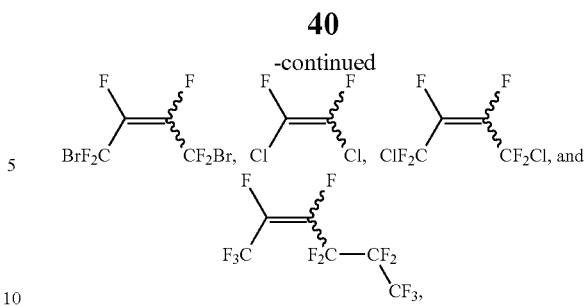

wherein Rf is a (per)fluorinated alkyl group having a carbon number of from 1 to 20, a (per)fluorinated alkyl group having a carbon number of from 1 to 20 and having an etheric oxygen atom between a carbon atom and a carbon atom, or a (per)fluorinated aryl group having a carbon number of from 5 to 20.

10. The production method according to claim 1, wherein the reaction is carried out at a temperature of from 0 to 150° C.

11. The production method according to claim 1, wherein the reaction is carried out in the absence of a solvent.

12. The production method according to claim 1, wherein the metal of the metal-carbene complex compound (10) is molybdenum or tungsten and the metal-carbene complex compound (10) has an imide ligand of formula =$NR^1$ where $R^1$ is an alkyl or aryl group.

13. The production method according to claim 1, wherein the metal-carbene complex compound (10) is at least one selected from the group consisting of

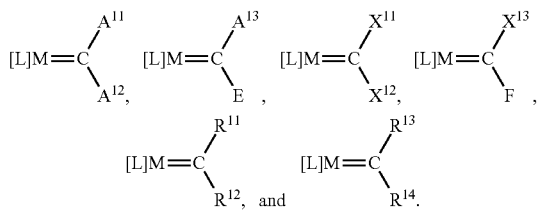

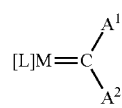

14. The production method according to claim 1, wherein the metal-carbene complex compound (10) has the following formula $$[L]M=C\begin{smallmatrix}A^1\\A^2\end{smallmatrix}$$

wherein $A^1$ and $A^2$ are each independently a hydrogen atom, a halogen atom, a monovalent hydrocarbon group having a carbon number of from 1 to 20, or a monovalent hydrocarbon group having a carbon number of from 1 to 20 and containing one or more atoms selected from the group consisting of an oxygen atom, a nitrogen atom, a sulfur atom, a phosphorus atom, and a silicon atom, wherein $A^1$ and $A^2$ may bond, as a divalent group formed by removing one hydrogen or halogen atom, to each other to form a ring.

* * * * *